US009145452B2

(12) United States Patent
Luo et al.

(10) Patent No.: US 9,145,452 B2
(45) Date of Patent: Sep. 29, 2015

(54) APPLICATION OF FIBRINOGEN-420 AND ITS ACTIVE DOMAIN

(71) Applicant: Tsinghua University, Beijing (CN)

(72) Inventors: Yongzhang Luo, Beijing (CN); Huadong Tang, Beijing (CN); Yan Fu, Beijing (CN)

(73) Assignee: Tsinghua University, Beijing (CN)

( * ) Notice: Subject to any disclaimer, the term of this patent is extended or adjusted under 35 U.S.C. 154(b) by 0 days.

(21) Appl. No.: 14/020,255

(22) Filed: Sep. 6, 2013

(65) Prior Publication Data
US 2014/0087441 A1    Mar. 27, 2014

Related U.S. Application Data

(63) Continuation of application No. 13/254,987, filed as application No. PCT/CN2010/000277 on Mar. 5, 2010, now abandoned.

(51) Int. Cl.
*C07K 14/75* (2006.01)
*A61K 38/36* (2006.01)

(52) U.S. Cl.
CPC ............... *C07K 14/75* (2013.01); *A61K 38/363* (2013.01)

(58) Field of Classification Search
None
See application file for complete search history.

(56) References Cited

FOREIGN PATENT DOCUMENTS

CN    1712413       12/2005
WO    WO-00/09562 A1    2/2000

OTHER PUBLICATIONS

Eszter, E. (2007) Arteriosclerosis, thrombosis, and vascular biology, (2007) vol. 27, No. 7, pp. 1657-1665 (Abstract only).*
Regezi, Joseph A. Modern Pathology (2002) vol. 15 (3), 331-341.*
Hao et al. Current protein & peptide science, (2015) vol. 16, No. 2, pp. 135-146 (Abstract only).*
Tang et al., "Fibrinogen has chaperone-like activity." *Biochem. Biophys. Res. Comm.* (Jan. 16, 2009 hard publication and Dec. 4, 2008 online pubklication) 378, 662-667.
Tang et al., $\alpha_E C$, the C-Terminal Extension of Fibrinogen, Has Chaperone-Like Activity. *Biochemistry* (Mar. 15, 2009 online publication) 48, 3967-3976.
Lei, T.H. CN 1712413A (Dec. 2005) Human assisted machine translation into English.
Applegate, D. et al., "The alpha-E-C domain of human fibrinogen-420 is a stable and early plasmin cleavage product", Blood, Apr. 1, 2000, 95(7):2297-2303, American Society of Hematology, Washington DC USA.

* cited by examiner

*Primary Examiner* — Nashaat Nashed
(74) *Attorney, Agent, or Firm* — Drinker Biddle & Reath LLP

(57) ABSTRACT

The invention provides the uses of fibrinogen-420 or alpha EC domain thereof, for inhibiting protein aggregation, refolding the denatured proteins, manufacturing drugs for prevention and/or treatment of protein misfolding diseases, resisting protein denaturation, and detecting the quality of protein products. The invention also provides the drugs for prevention and/or treatment of protein misfolding diseases or protein denatured disease, and the protein stabilizer. The active ingredient of the said drugs and stabilizer is fibrinogen-420 or alpha EC domain thereof.

9 Claims, 3 Drawing Sheets

SEQUENCE LISTING

```
<160> NUMBER OF SEQ ID NOS: 3

<210> SEQ ID NO 1
<211> LENGTH: 236
<212> TYPE: PRT
<213> ORGANISM: Homo sapiens

<400> SEQUENCE: 1

Asp Cys Asp Asp Val Leu Gln Thr His Pro Ser Gly Thr Gln Ser Gly
1               5                   10                  15

Ile Phe Asn Ile Lys Leu Pro Gly Ser Ser Lys Ile Phe Ser Val Tyr
            20                  25                  30

Cys Asp Gln Glu Thr Ser Leu Gly Gly Trp Leu Leu Ile Gln Gln Arg
        35                  40                  45

Met Asp Gly Ser Leu Asn Phe Asn Arg Thr Trp Gln Asp Tyr Lys Arg
    50                  55                  60

Gly Phe Gly Ser Leu Asn Asp Glu Gly Glu Gly Phe Trp Leu Gly
65                  70                  75                  80

Asn Asp Tyr Leu His Leu Leu Thr Gln Arg Gly Ser Val Leu Arg Val
                85                  90                  95

Glu Leu Glu Asp Trp Ala Gly Asn Glu Ala Tyr Ala Glu Tyr His Phe
            100                 105                 110

Arg Val Gly Ser Glu Ala Glu Gly Tyr Ala Leu Gln Val Ser Ser Tyr
        115                 120                 125

Glu Gly Thr Ala Gly Asp Ala Leu Ile Glu Gly Ser Val Glu Glu Gly
    130                 135                 140

Ala Glu Tyr Thr Ser His Asn Asn Met Gln Phe Ser Thr Phe Asp Arg
145                 150                 155                 160

Asp Ala Asp Gln Trp Glu Glu Asn Cys Ala Glu Val Tyr Gly Gly Gly
                165                 170                 175

Trp Trp Tyr Asn Asn Cys Gln Ala Ala Asn Leu Asn Gly Ile Tyr Tyr
            180                 185                 190

Pro Gly Gly Ser Tyr Asp Pro Arg Asn Asn Ser Pro Tyr Glu Ile Glu
        195                 200                 205

Asn Gly Val Val Trp Val Ser Phe Arg Gly Ala Asp Tyr Ser Leu Arg
    210                 215                 220

Ala Val Arg Met Lys Ile Arg Pro Leu Val Thr Gln
225                 230                 235

<210> SEQ ID NO 2
<211> LENGTH: 32
<212> TYPE: DNA
<213> ORGANISM: Artificial sequence
<220> FEATURE:
<223> OTHER INFORMATION: Primer
```

```
-continued

<400> SEQUENCE: 2
ggaattccat atggactgtg atgatgtcct cc                              32

<210> SEQ ID NO 3
<211> LENGTH: 30
<212> TYPE: DNA
<213> ORGANISM: Artificial sequence
<220> FEATURE:
<223> OTHER INFORMATION: Primer

<400> SEQUENCE: 3
accgctcgag ctattgggtc acaaggggcc                                 30
```

APPLICATION OF FIBRINOGEN-420 AND ITS ACTIVE DOMAIN

RELATED APPLICATIONS

This application is continuation of U.S. patent application Ser. No. 13/254,987, filed Mar. 14, 2012, which is a national stage application (under 35 U.S.C. §371) of PCT/CN2010/000277, filed Mar. 5, 2010, which claims priority to Chinese Application No. CN 200910079569.0, filed Mar. 6, 2009.

The Sequence Listing associated with this application is filed in electronic format via EFS-Web and hereby incorporated by reference into the specification in its entirety. The name of the text file containing the Sequence Listing is seqlist.txt. The size of the text file is 2,679 bytes and the text file was created on Aug. 14, 2014.

FIELD OF THE INVENTION

This invention relates to a novel application of Fibrinogen-420 and its active domain.

BACKGROUND OF THE INVENTION

Fibrinogen, also known as coagulation factor I, exists in the blood and is an important protein in the process of blood clotting. Fibrinogen has a molecular weight of 340,000 Daltons, and is composed of two subunits connected by disulfide bonds to form a dimer. Each subunit respectively consists of three intertwined polypeptide chains, called the A chain, the B chain, and the C chain. In the process of clotting, fibrinogen is digested by thrombin to generate fibrin and thus form an insoluble fibrin polymer. Then the blood fiber formed from the fibrin polymer and blood platelets will form a solid tampon. Fibrinogen is also a stress protein, whose content in the blood is about 1.5-4 mg/ml. The content of fibrinogen is related to the immune status, which could also reflect the risk of cardiovascular disease.

Fibrinogen-420 is a subtype of fibrinogen, in which the C-terminal of the A chain has an extension of globular domain as compared to the A chain of normal fibrinogen. This globular domain is called the alpha EC domain protein (SEQ ID NO:1) and has high homology with the globular domain at the terminus of the B and C chains. The molecular weight of fibrinogen-420 is about 420,000 Daltons, which is different from the normal tissue fibrinogens (340,000 Daltons).

Protein misfolding disease is a class of diseases which are due to the conformational change of specific protein(s) in the tissue, by which protein(s) aggregate(s) to produce amyloidosis, finally resulting in a class of diseases with pathological changes in tissues and organs, with examples including Alzheimer's disease and bovine spongiform encephalopathy. There have been no effective methods to prevent or treat these diseases by now. The existing methods, such as monoclonal antibody technology, small molecules, synthetic peptides, et al. have many disadvantages including immune rejection reactions, lacking of broad-spectrum, significant side effects, and a short half-life in vivo.

There are a large number of heat shock proteins or chaperones, protect cells from high temperature, free radicals, organic solvents (eg ethanol) and other damages when the body suffers from stimulation. But the heat shock proteins do not exist in the circulatory system. The mechanism by which the body protects extracellular protein is unclear.

DESCRIPTION OF THE INVENTION

The purpose of this invention is to provide novel applications of Fibrinogen-420 and its active domain.

The present inventors' study shows that fibrinogen-420 has molecular chaperone activity and broad-spectrum, non-specific protective effects. Fibrinogen-420 is a human endogenous protein, which will not be quickly degraded in vivo and will not trigger immune rejection. It can promote denatured proteins to refold properly and stabilize protein conformation and function. So it can be widely used in protein refolding, denatured protein testing in quality control, and prevention of protein denaturation, etc. The protein described could be a recombinant protein or natural protein.

A Fibrinogen-420 molecule contains alpha EC domain protein (SEQ ID NO:1), which when used alone has the same or similar function as intact Fibrinogen-420. The amino acid sequence of alpha EC domain is shown as SEQ ID NO.1. A specific example of fibrinogen-420 is human fibrinogen-420.

Fibrinogen-420 or alpha EC domain protein (SEQ ID NO:1) can be prepared into the protein reagent for use. Described protein reagents include at least fibrinogen-420 or alpha EC domain protein (SEQ ID NO:1), and the protein reagents do not rule out other solvents and additives. Good results are expected when the ratio of other protein(s) on which fibrinogen-420 or alpha EC domain protein (SEQ ID NO:1) actsvs. fibrinogen-420 or alpha EC domain protein (SEQ ID NO:1) is in the range of 25:1 to 1:100, among which the ratio of 1:1 is included. The best ratio depends on the requirement of specific application.

The present invention also shows that fibrinogen-420 or alpha EC domain protein (SEQ ID NO:1) can inhibit the aggregation of denatured proteins, and protect the protein activity as well. Thus it can be used as drugs to treat protein misfolding diseases.

The drugs to treat protein misfolding diseases contain fibrinogen-420 or alpha EC domain protein (SEQ ID NO:1) as the active ingredient. The drugs can be used for the treatment of a variety of protein misfolding diseases, such as protein denaturation caused by fever, tobacco, alcohol, oxygen free radicals and other harmful substances.

The drugs for the treatment of protein misfolding diseases contain fibrinogen-420 or alpha EC domain protein (SEQ ID NO:1) as the active ingredient.

The fibrinogen-420 or alpha EC domain protein (SEQ ID NO:1) of the present invention can catch the protein unfolding process. By helping the protein to refold correctly or keeping it in a folded state, fibrinogen-420 or alpha EC domain protein can prevent protein aggregation and stabilize the activity and function of a protein. Thus, fibrinogen-420 or alpha EC domain protein (SEQ ID NO:1) can enhance the ability of a protein against denaturation, so that it can be used as a protein stabilizing agent in vitro.

The aforementioned protein stabilizing agent described contains fibrinogen-420 or alpha EC domain protein (SEQ ID NO:1) as the active ingredient. The protein stabilizing agent described can inhibit the aggregation of proteins which are prone to aggregation and precipitation. The protein stabilizing agent can also protect the enzyme activity, such as by stabilizing the activity of citrate synthase, luciferase, insulin and other enzymes.

FIGURES

EXAMPLES

Example 1

Figure 1:
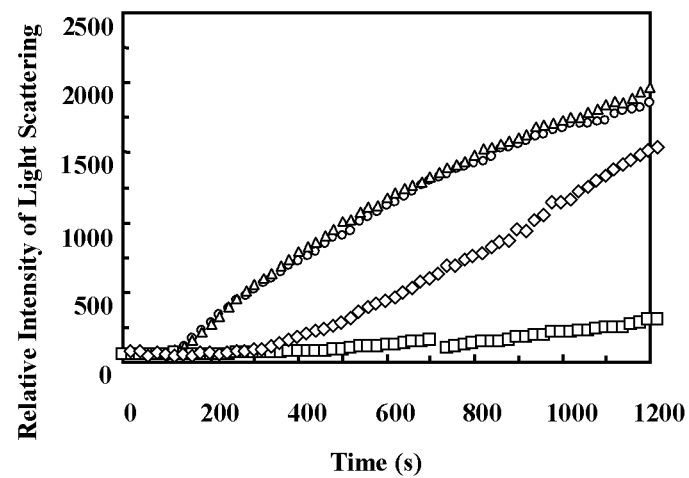
FIG. 1 shows that Fibrinogen-420 or alpha EC domain protein (SEQ ID NO:1) inhibited the thermal-induced denaturation and aggregation of citrate synthase.

Fibrinogen-420 and Alpha EC Domain Protein (SEQ ID NO:1) Inhibited the Denaturion and Aggregation of Citrate Synthase a. Preparation of Fibrinogen-420 and Alpha EC Domain Protein (SEQ ID NO:1)

Blood or cord blood was purified to obtain mixed fibrinogen, from which fibrinogen-420 was further purified. The process was as follows:

(1) Purification of the mixed fibrinogen: first, a protease inhibitor was added into fresh blood or cord blood, followed by centrifugation at 4° C., 2000 rpm. The supernatant was isolated to obtain light yellow plasma. Glycine (dry powder) was added to the plasma under stirring to make glycine completely dissolved to a final concentration of 2.1 M. A white flocculent precipitate was obtained, which was then centrifuged at 5000 rpm for 15 min. The obtained precipitate was dissolved in a buffer solution (0.15 M NaCl, 0.01 M sodium phosphate, pH 6.4) in a volume of ⅓ of the volume of the original plasma. The step was repeated until the volume after dissolution reached 1/10 of volume of the original plasma. An equal volume of pure water was added for dilution. The diluted solution was kept at 2-5° C. for 6 hours, and then subjected to centrifugation for removing the precipitate. An equal volume of 0.3 M sodium chloride solution was added to the supernatant, and then 95% ethanol added to a final concentration of 8% ethanol (ratio in volume). At the same time, the temperature was reduced to −3° C. After complete precipitation, centrifugation was performed at 5000 rpm to obtain a precipitate to be used as raw materials in the next step for the purification of fibrinogen-420.

(2) Purification of fibrinogen-420: the obtained fibrinogen precipitate was dissolved in 0.3 mol/L sodium chloride solution and dialyzed against 0.005 mol/L Tris-phosphate buffer, pH8.6 (the molar concentration was calculated on the basis of phosphate group). Mono Q HR 10/10 anion exchange column (Pharmacia) was used as the chromatographic column. A stepwise pH elution was performed to elute the sample, which started from 0.005 mol/L Tris-phosphate buffer, rapidly changed to 0.2 mol/L Tris-phosphate buffer, pH 6.0, and then maintained as 0.2 mol/L Tris-phosphate buffer, pH 6.0 for 12 column volumes for elution. Finally a linear gradient elution was performed for 12 column volumes, to 0.5 mol/L Tris-phosphate buffer, pH 4.2. Fibrinogen-420 was obtained in the last linear elution step. The protein was subjected to dialysis against 125 mmol/L sodium chloride, 25 mmol/L HEPES buffer (pH 7.4), and then stored therein.

Alpha EC domain protein (SEQ ID NO:1) was obtained as follows:

Refolding and purification of the alpha EC domain protein (SEQ ID NO:1): PCR amplification was performed with a human liver cDNA library as the template. The sequences of primers were as follows:

(SEQ ID NO: 2)
5-GGAATTCCATATGGACTGTGATGATGTCCTCC-3'

(SEQ ID NO: 3)
5-ACCGCTCGAGCTATTGGGTCACAAGGGGCC-3'

Restriction sites of NdeI and XhoI were introduced into the primers. The annealing temperature of PCR amplification was 55° C. The $\alpha_E C$ fragment was digested with restriction enzymes of NdeI and XhoI, and ligated to pET-30a expression vector (Novagen Inc.) which had been double-digested by the same enzymes. The constructed recombinant expression vector was transformed into competent E. coli cells BL21/DE3 (Beijing DingGuo Biotechnology Company), resulting in recombinant bacteria. Monoclonal recombinant bacteria were picked, inoculated to 10 ml LB medium (with 100 μg/ml kanamycin), incubated overnight and then transferred to 1 liter of LB medium (with 100 μg/ml kanamycin). Once the turbidity of the medium ($OD_{600}$) reached about 0.8, 0.5 mM IPTG was added for induction for 4 hours, and then the bacteria were collected by centrifugation. The collected bacteria were disrupted and then the inclusion body protein was collected. The inclusion body protein was dissolved, restored, and then subjected to purification by anion-exchange column. The sample loading buffer was as follows: 8M urea, 20 mM Tris-HCl and pH8.0, 30 mM BME. The elution buffer was prepared by adding 1M NaCl to the loading buffer. A linear gradient was used for elution and the elution peaks were collected stepwise. The purity of the protein was detected by electrophoresis. Components, the purity of which was greater than 80%, were selected for the refolding experiments.

During the refolding, the protein was adjusted to a concentration of less than 0.2 mg/ml by 20 mM Tris-HCl buffer containing 8 M urea (pH 8.0), and then dialyzed against 20 mM Tris-HCl, 150 mM NaCl, 1 mM calcium chloride, pH 8.0. The dialysis liquid was changed at an interval of at least 4 hours, and the refolding solution was changed at least twice. The dialysis was performed completely overnight. Finally, the protein was dialyzed against 20 mM Tris-HCl loading buffer, ready for the purification of the refolded protein. The purification was performed using an anion exchange column. Before loading onto the column, the sample was centrifuged, or filtered with 0.22 micron pore-sized membrane. A linear salt ion gradient was used for elution, and the protein peaks were collected stepwise. The purity was detected by oxide gel electrophoresis.

b. Fibrinogen-420 and Alpha EC Domain Protein (SEQ ID NO:1) Inhibited the Thermal Denaturation and Aggregation of Citrate Synthase Citrate synthase is a key enzyme in the tricarboxylic acid cycle, however its thermal stability is poor. The temperature of 43° C. will cause its denaturation, aggregation and thus precipitation in vitro. The process of citrate synthase aggregation can be indicated by the change of light scattering. The method was as follows:

The process of light scattering was detected with FL4500 florescence spectrometer (Hitachi instrument), with both the exciting light and emission light adjusted to 500 nm and slit width to 2.5 nm. The citrate synthase was dissolved in 40 nM HEPES buffer solution to the final concentration of 0.15 μM. Simultaneously, 0.15 μM fibrinogen-420 was added for the experiment group 1, and 0.15 μM alpha EC domain protein (SEQ ID NO:1) was added for the experiment group 2. The equal volume of HEPES buffer solution was added for the control group 1 and the equal volume of 1.2 μM bovine serum albumin was added for the control group 2. The samples were placed in a 43° C. water bath and the signal of light scattering was detected. The experiment was repeated for 3 times.

The result of the light scattering signal detection was shown in FIG. 1, which indicated that during the process of heating for 200 s, the citrate synthase in the control group 1 and 2 started to aggregate and the increase of the intensity of light scattering could be detected. However, in the experiment group 1 and 2, citrate synthase aggregation was reduced obviously. In the experiment group 2, the effect of inhibition on the thermal-denatured aggregation of citrate synthase was better than that in group 1. In the experiment group 2, 0.15 μM alpha EC domain protein (SEQ ID NO:1) could almost totally inhibit the thermal denaturation and aggregation process of equal molar citrate synthase at 43° C.

In FIG. 1, (○) represents control group 1, (●) represents control group 2, (Δ) represents experiment 1, (□) represents example 2.

c. Fibrinogen-420 and Alpha EC Domain Protein (SEQ ID NO:1) Inhibited the Chemical Denaturation and Aggregation of Citrate Synthase.

Under the condition of guanidine hydrochloride and reducing agent (6 M guanidine hydrochloride, 10 mM DTT, incubated at room temperature for 2 hours), citrate synthase was completely denatured, and then diluted with 40 mM HEPES buffer to a final concentration of 0.15 μM. Simultaneously, 0.3 μM alpha EC domain protein (SEQ ID NO:1) was added for the experiment group 1, 0.6 μM alpha EC domain protein (SEQ ID NO:1) was added for the experiment group 2. The equal volume of HEPES buffer solution was added for the control group 1, and the equal volume of 1.2 μM bovine serum albumin was added for the control group 2. Then the light scattering signal of each sample was detected. The experiment was repeated for 3 times. The process of light scattering was detected with a FL4500 florescence spectrometer (Hitachi instrument), with both the exciting light and emission light adjusted to 500 nm and slit width to 2.5 nm.

Figure 2:
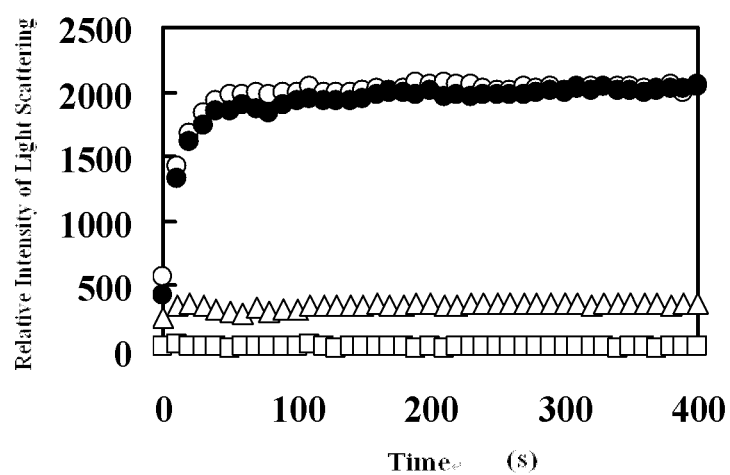
FIG. 2 shows that the alpha EC domain protein (SEQ ID NO:1) inhibited the chemical denaturation and aggregation of citrate synthase.

The result of the light scattering signal detection was shown in the FIG. 2, which indicated that the aggregation process was changed significantly in the experiment groups compared with the control groups. Moreover, 0.3 μM alpha EC could inhibit aggregation obviously, and 0.6 μM alpha EC could almost completely inhibit aggregation.

In FIG. 2, (○) represents control group 1, (●) represents control group 2, (Δ) represents experiment 1, and (□) represents adding 0.6 μM alpha EC.

Example 2

Fibrinogen-420 and Alpha EC Domain Protein Protected the Activity of Citrate Synthase (CS)

The following experimental method was carried out which showed that fibrinogen-420 and alpha EC domain protein (SEQ ID NO:1) inhibited the thermal denaturation and inactivation of citrate synthase (CS).

Citrate synthase was dissolved in a 40 mM HEPES buffer solution to the final concentration of 0.075 μM. Simultaneously, 0.075 μM fibrinogen-420 was added for the experiment group 1; 0.15 μM fibrinogen-420 was added for the experiment group 2; 0.075 μM alpha EC domain protein (SEQ ID NO:1) was added for the experiment group 3; 0.15 μM alpha EC domain protein (SEQ ID NO:1) was added for the experiment group 4, and the equal volume of HEPES buffer solution was added for the control group. The samples were placed into a 43° C. water bath, and simultaneously the change of the citrate synthase activity was detected. The activity of citrate synthase before heating was defined as 100%.

The method for detecting the activity of citrate synthase was as follows:

930 μL of TE buffer solution (50 nM Tris, 2 mM EDTA, pH 8.0), 10 μL 10 mM oxaloacetic acid, 10 μL 10 mM DTNB, 30 μL 5 mM acetyl-CoA, were mixed. Then 20 μL solution containing citrate synthase was added into the mixed solution quickly and the dynamic change of UV absorption was detected immediately at the wavelength of 412 nm. The slope the linear curve of absorbency change represents the activity of the enzyme.

The detection result of the citrate synthase activity was shown in FIGS. 6 and 7, which indicated that as time lapsed, the activity of citrate synthase in the control group decreased rapidly whereas the rate of activity loss could be slowed effectively in all experiment groups.

Figure 3:
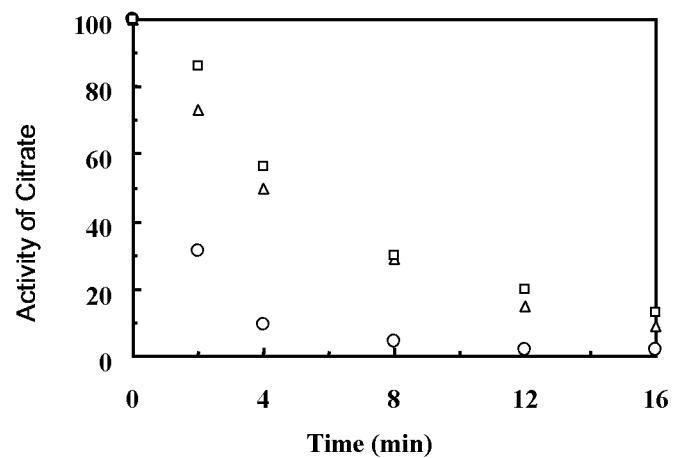
FIG. 3 shows that Fibrinogen-420 inhibited the thermal-induced denaturation and inactivation of citrate synthase.
Figure 4:
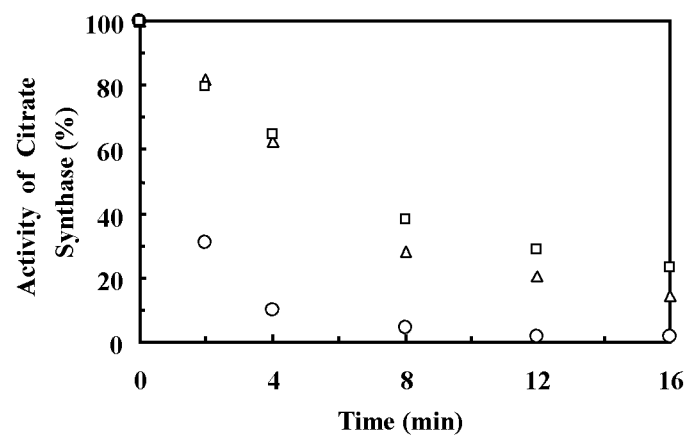
FIG. 4 shows that the alpha EC domain protein (SEQ ID NO:1) inhibited the thermal-induced denaturation and inactivation of citrate synthase.

In FIG. 3, (○) represents control group, (Δ) represents experiment group 1, (□) represents experiment group 2. In FIG. 4, (○) represents control group, (Δ) represents experiment group 3, (□) represents experiment group 4.

Example 3

Alpha EC Domain Protein (SEQ ID NO:1) Recognized Denatured Citrate Synthase Specifically Citrate synthase and alpha EC domain protein (SEQ ID NO:1) were incubated together at the temperature of 43° C. for 5 min or 10 min. Then an antibody against citrate synthase and an antibody against alpha EC domain protein (SEQ ID NO:1) were respectively added into the supernatants, to perform co-immunoprecipitation. In the control group, citrate synthase and alpha EC domain protein (SEQ ID NO:1) were incubated together at room temperature and an antibody against citrate synthase and an antibody against alpha EC domain protein (SEQ ID NO:1) were respectively added into the supernatants to perform co-immunoprecipitation.

Figure 5:
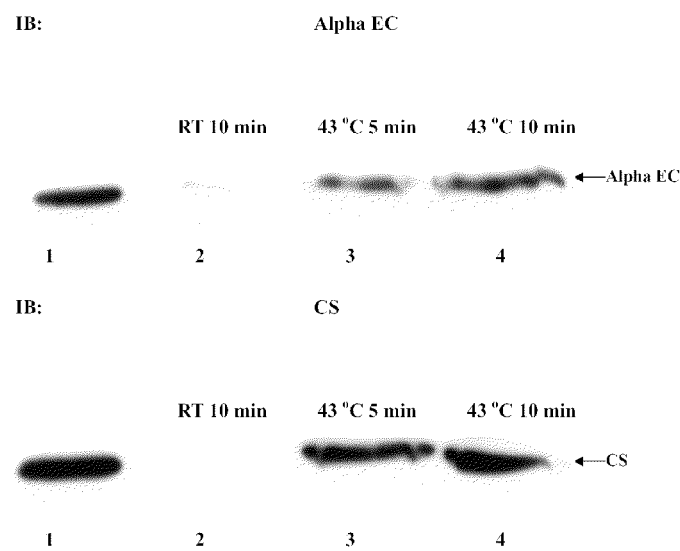
FIG. 5 shows that the alpha EC domain protein (SEQ ID NO:1) specifically recognized the denatured citrate synthase protein.

Results were shown in FIG. 5, which indicated that after the addition of the antibody against citrate synthase, the denatured citrate synthase could be precipitated and alpha EC domain protein (SEQ ID NO:1) could also be precipitated at the same time. After the addition of the antibody against alpha EC domain protein (SEQ ID NO:1), both alpha EC domain protein (SEQ ID NO:1) and citrate synthase could be precipitated. The above experimental results indicated that after heating, citrate synthase and alpha EC domain protein (SEQ ID NO:1) formed a complex so that the antibody against one protein could precipitate the other protein at the same time. In the control group, co-immunoprecipitation did not occur. The result illustrated that alpha EC domain protein (SEQ ID NO:1) could specifically recognize and bind to the thermally denatured citrate synthase.

In FIG. 5, the upper panel showed the co-immunoprecipitation performed with the antibody against citrate synthase, which was detected with the antibody against alpha EC domain protein (SEQ ID NO:1) after electrophoresis. Lane 1 represented the positive control. Lane 2 represented co-immunoprecipitation after incubation for 10 min at room temperature. Lane 3 and 4 represented co-immunoprecipitation after being heated at 43° C. for 5 min and 10 min respectively. The lower panel of the figure showed the co-immunoprecipitation performed with the antibody against alpha EC domain protein (SEQ ID NO:1), which was detected with the antibody against citrate synthase after electrophoresis. Lane 1 represented the positive control of citrate synthase. Lane 2 represented the co-immunoprecipitation after incubation at room temperature for 10 min. Lane 3 and 4 represented co-immunoprecipitation after being heated at 43° C. for 5 min and 10 min respectively. In this figure, "CS" represents citrate synthase and "alpha EC" represents alpha EC domain protein (SEQ ID NO:1).

THE INDUSTRIAL PRACTICABILITY

The present invention provides novel uses of fibrinogen-420 and its active domain. In a biological diagnostic kit, particularly in an ELISA immunoassay diagnostic kit, the stability of an antibody cross-linked with a reporter enzyme (such as horseradish peroxidase, alkaline phosphatase or luciferase) is decreased. However, the addition of fibrinogen-420 or alpha EC domain protein (SEQ ID NO:1) can increase the shelf life of the product and the stability of the protein reagent, thus improving the product quality. Fibrinogen-420 or alpha EC domain protein (SEQ ID NO:1) can also be used to identify the unfolding and denatured protein, therefore it can be applied in the detection and the quality control of a protein product.

The invention claimed is:

1. A composition of matter comprising:
   (i) a protein having the amino acid sequence of SEQ ID NO: 1; and
   (ii) a target protein which needs to be stabilized and whose shelf life needs to be increased, wherein the target protein is citrate synthase, luciferase or insulin.

2. A method of inhibiting aggregation or denaturation of a protein product comprising citrate synthase, luciferase or insulin, comprising contacting a protein having the amino acid sequence of SEQ ID NO: 1 with said protein product, wherein aggregation or denaturation of the protein product is inhibited.

3. The method of claim 2, wherein the molar ratio of the protein having the amino acid sequence of SEQ ID NO: 1 to the protein product is from 25:1 to 1:100.

4. A method of treating a protein misfolding disease in a subject, comprising administering to the subject an effective amount of a protein having the amino acid sequence of SEQ ID NO: 1, wherein the protein misfolding disease is selected from the group consisting of Alzheimer's disease, Spinocerebellar ataxia, Parkinson's disease, Huntington's disease, familial amyotrophic lateral sclerosis, emphysema and bovine spongiform encephalopathy.

5. A method of detecting unfolded or denatured target protein in a sample of protein product comprising citrate synthase, luciferase or insulin, comprising the step of contacting a protein having the amino acid sequence of SEQ ID NO: 1 with said sample, wherein formation of a complex comprising the protein having the amino acid sequence of SEQ ID NO: 1 and the target protein indicates the presence of an unfolded or denatured target protein in said sample.

6. The method of claim 4, wherein the protein misfolding disease is Alzheimer's disease.

7. The method of claim 4, wherein the protein misfolding disease is bovine spongiform encephalopathy.

8. A biological or diagnostic kit comprising:
   (i) a protein having the amino acid sequence of SEQ ID NO: 1 as a stabilizer; and
   (ii) a target protein which needs to be stabilized and whose shelf life needs to be increased, wherein the target protein is citrate synthase, luciferase, insulin, or an antibody cross-linked to a reporter enzyme.

9. The kit according to claim 8, wherein the target protein is citrate synthase, luciferase or insulin.

* * * * *